United States Patent

Nanba et al.

[11] Patent Number: 6,063,391
[45] Date of Patent: May 16, 2000

[54] LIPSTICK COMPOSITION

[75] Inventors: Tomiyuki Nanba; Kazunori Yamazaki; Kuniko Takabayashi; Kunihiko Yoshida; Teruhiko Hineno; Tetsuji Nakamura; Koichi Nakamura; Katsuyuki Kaneko; Satoshi Tomomasa, all of Yokohama, Japan

[73] Assignee: Shiseido Co., Ltd., Tokyo, Japan

[21] Appl. No.: 08/867,022

[22] Filed: May 30, 1997

[30] Foreign Application Priority Data

Aug. 26, 1996 [JP] Japan .................................. 8-242699
Dec. 9, 1996 [JP] Japan .................................. 8-344622

[51] Int. Cl.[7] .............................. A61K 6/00; A61K 7/00; A61K 7/025
[52] U.S. Cl. .............................................. 424/407; 424/64
[58] Field of Search .............................. 424/64, 401, 486

[56] References Cited

U.S. PATENT DOCUMENTS

| | | | |
|---|---|---|---|
| 4,712,571 | 12/1987 | Remz et al. | 132/88 |
| 5,023,075 | 6/1991 | Macchio et al. | 424/63 |
| 5,444,096 | 8/1995 | McCrea et al. | 514/770 |
| 5,468,477 | 11/1995 | Kumar et al. | 424/78.17 |

FOREIGN PATENT DOCUMENTS

| | | |
|---|---|---|
| 0602905A2 | 12/1992 | European Pat. Off. . |
| 0602905A | 6/1994 | European Pat. Off. . |
| 0661042A2 | 12/1994 | European Pat. Off. . |
| 0640644A | 1/1995 | European Pat. Off. . |
| 0661042A | 5/1995 | European Pat. Off. . |
| 0657486A | 6/1995 | European Pat. Off. . |
| 2681245A | 3/1993 | France . |
| 4419354A | 12/1994 | Germany . |
| WO9618375A | 6/1996 | WIPO . |
| WO9619185A | 6/1996 | WIPO . |

*Primary Examiner*—Thurman K. Page
*Assistant Examiner*—Sharon Howard
*Attorney, Agent, or Firm*—Townsend & Banta

[57] ABSTRACT

A lipstick composition containing a nonaqueous polymer dispersion in which the polymer is dispersed in a volatile silicone and perfluoroalkyl denaturated silicone or perfluoroalkyl denaturated methylphenyl polysiloxane with a specific structure. Also a lipstick composition containing volatile silicone oil and or volatile hydrocarbon oil and perfluoroalkyl denaturated silicone and or perfluoroalkyl denaturated methylphenyl polysiloxane with a specific structure.

7 Claims, No Drawings

LIPSTICK COMPOSITION

RELATED APPLICATION

This application claims the priority of Japanese Patent applications No. 8-242699 filed on Aug. 26, 1996 and No. 8-344622 filed on Dec. 9, 1996, which are incorporated herein by reference.

BACKGROUND OF THE INVENTION

1. Field of the Invention

This invention relates in general to a lipstick composition, and more particularly to a lipstick composition which spreads smoothly and is easily applied on the lips, is not sticky, has a nice gloss on the lips, has a long lasting cosmetic effect, and whose color does not transfer onto coffee cups, clothes, etc.

2. The Prior Art

Conventionally, a usual oil-based lipstick has been composed of various oils, waxes and coloring materials, and had a nice gloss when applied on the lips but it had a shortcoming in that color transfer onto coffee cups, clothes, etc. occurred and that the cosmetic effect did not last long.

Various investigations have been conducted in order to eliminate this shortcoming and improve the long-lasting effect. For example, Japanese unexamined patent publication Tokkai Hei 5-178722 discloses an oil-based solid cosmetic(s) (oil-based makeup cosmetics and lipsticks) with a superior long-lasting effect containing one or more types of polyoxyalkylene denaturated organopolysiloxane, Tokkai Hei 6-199630 discloses an anti-color transfer cosmetic composition(s) (makeup cosmetic compositions and lipsticks) containing a volatile solvent, silicone resin, wax, powder and oil components, Tokkai Hei 6-298623 discloses lip-care cosmetic compositions with superior durability and friction resistance containing a specific alkylmethyl polysiloxane, Tokkai Hei 7-17831 discloses an oil-based cosmetic(s) (lipsticks) with a superior long-lasting effect containing a non-ionic surfactant with additional polymerization using ethylene oxide, a liquid oil agent(s) with perfluoroalkyl groups, liquid oil, semi-solid fat or solid fat and a pigment(s), and Tokkai Hei 7-33622 discloses an oil-based cosmetic(s) (lipsticks) with a superior long-lasting effect containing a polyoxyalkylene denaturated silicone, a liquid oil agent(s) with perfluoroalkyl groups, liquid oil, semi-solid fat or solid fat and a pigment(s).

Also, Japanese examined patent publication Tokko Sho 61-12884 discloses a makeup cosmetic(s) with a superior long-lasting effect containing, as a film forming ingredient, a nonaqueous polymer dispersion in which a dispersion polymer is dispersed in an organic solvent which does not dissolve it.

However, although these lipstick compositions are functional to a certain degree in terms of ease of application, stickiness and gloss, they do not exhibit sufficient effects in terms of being long lasting enough to prevent color transfer onto coffee cups, clothes, etc. and at the same time have a nice gloss on the lips.

BRIEF SUMMARY OF THE INVENTION

The object of the present invention is to provide a lipstick composition which spreads smoothly and is easy to apply on the lips, is not sticky before and after drying, has a nice gloss on the lips, has an extremely long lasting cosmetic effect, and whose color does not transfer onto coffee cups, clothes, etc.

The inventors conducted earnest research to address This problem and completed the present invention by making a new discovery to the effect that a lipstick composition which contained a nonaqueous polymer dispersion in which the polymer was dispersed in a volatile silicone and perfluoroalkyl denaturated silicone or perfluoroalkyl denaturated methylphenyl polysiloxane spread smoothly and was easy to apply on the lips, had a nice gloss on the lips, prevented stickiness, and had a long lasting cosmetic effect such that color did not transfer onto coffee cups, clothes, etc.

Furthermore, the inventors conducted earnest research to address this problem and completed the present invention by making a new discovery to the effect that a lipstick composition which contained organic silicone resin dissolved in volatile silicone or volatile hydrocarbon and a specific perfluoroalkyl denaturated silicone and/or perfluoroalkyl denaturated methylphenyl polysiloxane spread smoothly and was easy to apply on the lips, had a nice gloss on the lips and had a long lasting cosmetic effect such that color did not transfer onto coffee cups, clothes, etc.

The present invention provides a lipstick composition containing a nonaqueous polymer dispersion in which the polymer is dispersed in a volatile silicone and perfluoroalkyl denaturated silicone represented by the following general formula (1):

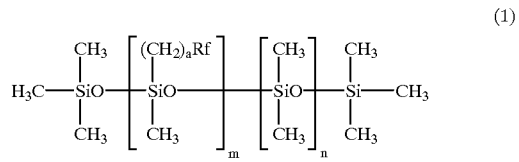

where, Rf denotes a perfluoroalkyl group with a carbon number of 1–12, a is an integer 0–5, and m and n are average numbers wherein m is 1–500 and n is 0–500.

The present invention also provides a lipstick composition containing a nonaqueous polymer dispersion in which the polymer is dispersed in a volatile silicone and perfluoroalkyl denaturated methylphenyl polysiloxane represented by the following general formula (2):

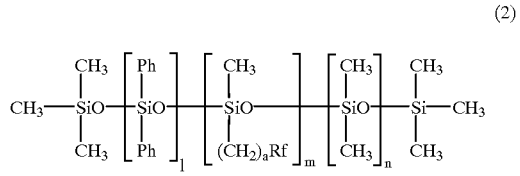

where, Rf denotes a perfluoroalkyl group with a carbon number of 1–12, a is an integer 0–5, and l, m and n are average numbers wherein l is 1–150, m is 1–150 and n is 0–150.

The present invention also provides the lipstick composition described above wherein said polymer is a polymer of an acrylic ester or methacrylic ester or a copolymer of an acrylic ester and mothacrylic ester.

The present invention also provides the lipstick composition described above wherein said nonaqueous polymer dispersion additionally has sucrose benzoate dispersed in it.

The present invention also provides the lipstick composition described above wherein said volatile silicone is one or more types of volatile silicone represented by the following general formula (3):

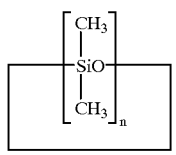

(3)

(n denotes an integer 3–7) or the following general formula (4):

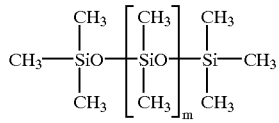

(4)

where m denotes an integer 0–5.

The present invention also provides a lipstick composition containing 1–70 wt % of organic silicone resin represented by the following average formula (5):

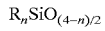 (5)

(R denotes a hydrocarbon group with a carbon number of 1–6 or a phenyl group, and n denotes a value in the range of 1.0–1.8), 2–98 wt % of volatile silicone oil represented by the following general formula (6):

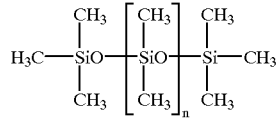

(6)

(n denotes an integer 0–3) or the following general formula (7):

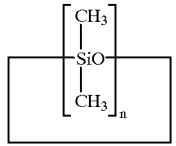

(7)

(n denotes an integer 3–8) and or volatile hydrocarbon oil whose boiling point at the atmospheric pressure is 60–260° C. and 2–50 wt % of perfluoroalkyl denaturated silicone represented by the following general formula (8):

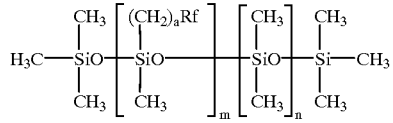

(8)

where, Rf denotes a perfluoroalkyl group with a carbon number of 1–12, a is an integer 0–5, and m and n are average numbers wherein m is 1–150 and n is 0–500.

The present invention also provides a lipstick composition containing 1–70 wt % of organic silicone resin represented by the following average formula (9):

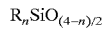 (9)

(R denotes a hydrocarbon group with a carbon number of 1–6 or a phenyl group, and n denotes a value in the range of 1.0–1.8), 2–98 wt % of volatile silicone oil represented by the following general formula (10):

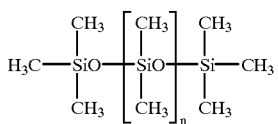

(10)

(n denotes an integer 0–3) or the following general formula (11):

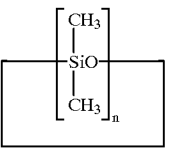

(11)

(n denotes an integer 3–8) and/or volatile hydrocarbon oil whose boiling point at the atmospheric pressure is 60–260° C. and 2–50 wt % of perfluoroalkyl denaturated methylphenyl polysiloxane represented by the following general formula (12):

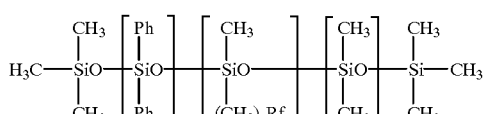

(12)

where, Rf denotes a perfluoroalkyl group with a carbon number of 1–12, a is an integer 0–5, and l, m and n are average numbers wherein l is 1–150, m is 1–150 and n is 0–150.

DETAILED DESCRIPTION

First, the present invention as described in claims 1–5 is described in detail below.

A significant difference between the lipstick composition of the present invention and said Tokko Sho 61-12884 publication lies in the fact that, whereas said publication uses, for the organic medium, a lower alcohol such as ethanol, propanol or isopropanol, an aliphatic hydrocarbon such as mineral spirits, Isoper (from Esso Sekiyu K.K.) or IP solvent (from Idemitsu petroleum), and an aromatic hydrocarbon or a mixture thereof, the present invention uses, for the medium (outer phase), volatile silicone which has superior characteristics in terms of odor and skin safety compared to said medium.

Also, Tokko Sho 61-12884 is related particularly to eyeliners, mascaras, eyebrow liners and nail polish among makeup cosmetics and no other examples are disclosed. On the other hand, the present invention is related particularly to a lipstick composition among makeup cosmetics.

The nonaqueous polymer dispersion mentioned in the present invention is a resin solution which is the polymer dispersed in a volatile silicone medium. This can typically be prepared by polymerizing a polymerizing monomer in a volatile silicone solvent. Any polymerizing monomer can be used, but a radical polymerizing monomer is particularly preferable. Preparation can be done by means of radical polymerization of it in the volatile silicone solvent using a radical polymerization initiator. It is also possible to use a polymer polymerized by means of any method such as anion polymerization, cation polymerization and radical polymerization and disperse it in volatile silicone in a stable fashion. However, the dispersion prepared by the aforementioned polymerization method is more preferable in terms of dispersion stability. The composition ratio of the polymer and the volatile silicone in the nonaqueous polymer dispersion is not limited, but a preferable range is (polymer):(volatile silicone)=1:25-6:1, and a more preferable range is 1:7–2:1.

The type of the polymer contained in the nonaqueous polymer dispersion in the lipstick composition of the present invention is not limited. For example, a polymer whose monomer is an ester between acrylic acid or methacrylic acid and alcohol with a carbon number of 1–10, an acrylic or methacrylic silicone ester polymer, and a polymer of styrene, α-methylstyrene, vinyl acetate or vinyl propionate can be used. Both a homopolymer and copolymer can be used. More preferable is an acrylic ester or methacrylic ester polymer, or a copolymer of acrylic ester and methacrylic ester.

For the nonaqueous polymer dispersion, it is preferable to disperse sucrose benzoate in addition to the aforementioned polymer in the volatile silicone.

The nonaqueous polymer dispersion contained in the lipstick composition of the present invention uses, for the medium to disperse the polymer, a volatile silicone which has superior characteristics in terms of odor and skin safety. Selection of the medium is not limited as long as it is a volatile silicone. Preferable is a volatile silicone represented by the above general formulas (3) and (4).

The amount of nonaqueous polymer dispersion to be blended is preferably 20–80 wt %, more preferably 40–60 wt %, of the total lipstick composition. If the amount is less than 20 wt %, then color transfer onto coffee cups, clothes, etc. occurs and the long-lasting effect is poor. An amount more than 80 wt % is not preferable because then ease of application would be poor.

Perfluoroalkyl denaturated silicone or perfluoroalkyl denaturated methylphenyl polysiloxane contained in the lipstick of the present invention is one or more types represented by the above general formula (1) or (2), and the amount is preferably 5–30 wt %, more preferably 10–20 wt %, of the total lipstick composition. If the amount is less than 5%, then stickiness (immediately after to three hours after application) is a problem. An amount more than 30% is not preferable because then the film forming ability of the nonaqueous polymer dispersion with a volatile silicone medium of the present invention would be impeded and color transfer onto coffee cups and clothes occurs, resulting in a poor long-lasting effect. Both the aforementioned perfluoroalkyl denaturated silicone or perfluoroalkyl denaturated methylphenyl polysiloxane can be contained in the same type.

In addition to the aforementioned essential ingredients to obtain the effects of spreading smoothly and easily applied on the lips, not being sticky, having a nice gloss on the lips, having a long lasting cosmetic effect, and not causing color transfer onto coffee cups, clothes, etc., the lipstick composition of the present invention can contain other ingredients normally used in cosmetics and medicinal drugs as necessary within a qualitative and quantitative range where the effects of the present invention are not degraded. Examples include ion exchange water, dimethyl polysiloxane, methylphenyl polysiloxane, dimethylsiloxane-methylphenylsiloxane copolymers, high polymer gum-like dimethyl polysiloxane, silicones such as amino denaturated silicone and polyether denaturated silicone, animal oils such as lanolin, plant oils such as castor oil and olive oil, synthetic ester oils such as isopropyl myristate and glycerol tri-2-ethylhexanoate, waxes such as carnauba wax, candelilla wax, bees wax and hydrocarbon types, polyhydric alcohol-type humectants such as glycerine, propylene glycol and 1,3 butylene glyco, various surfactants, thickeners, gelation agents, metal soaps, aqueous polymers, oil soluble polymers, drugs, antioxidants, pigments, dyes, pearl agents, organic/inorganic powders and perfumes.

The lipstick composition of the present invention is prepared by heating the composition ingredients including the aforementioned essential ingredients, stirring and mixing them, followed by cooling. The lipstick composition of the present invention can be in any form. For example, it can be solid (stick and such), semi-solid and liquid. It can also be a W/O emulsion.

Next, the present invention as described in claims 6–7 is described in detail. The organic silicone resin which is used in the present invention, represented by [Chemical formula 25], has, for its molecular configuration unit, an appropriate combination of $R_3SiO_{1/2}$ units, $R_2SiO$ units, $RSiO_{3/2}$ units and $SiO_2$ units. Their ratio is chosen such that the average formula (13):

$$R_nSiO_{(4-n)/2} \qquad (13)$$

(R denotes a hydrocarbon group with a carbon number of 1–6 or a phenyl group, and n denotes a value in the range of 1.0–1.8) is satisfied. It is preferable to have an average molecular weight of appropriately 1,500–100,000.

The aforementioned organic silicone resin is soluble in benzene and can be prepared by various methods. For example, a compound represented by the general formulas $R_3SiX$, $R_2SiX_2$, $RSiX_3$ and $SiX_4$ (X denotes a hydrolyzable group such as groups including chlorine, bromine and fluorine, alkoxy groups including methoxy and ethoxy groups and acyloxy groups) is added to an appropriate solvent for the resin composition such as benzene, toluene and xylene, and then this solvent is added to water, the amount of which is enough to obtain the desired hydrolysis and co-condensation in an appropriate acidic solvent. From the two-phase system thus obtained, the water phase is removed and the remaining resin-like substance is neutralized by a sufficient amount of sodium bicarbonate or another alkaline substance. The solvent is then removed to obtain the target organic silicone resin.

The organic silicone resin of the present invention can be obtained in the form of a volatile silicone oil or a dimethyl polysiloxane solution. Examples include KF7312F, KF7312J, KF7312K, KF9001 and KF9002 (from Shin-Etsu Chemical Co., Ltd.), DC593 and BY11-018 (from Toray Dow-Corning Silicone Co., Ltd.) and TSF4600 (from Toshiba Silicone Co., Ltd.).

The amount of the organic silicone of the present invention to be blended is 1–70 wt %, preferably 5–50 wt %, and more preferably 5–30 wt %. If it is less than 1 wt %, then the long-lasting effect is insufficient. If it is more than 70 wt %, then stickiness becomes a problem when used.

The volatile silicone oils represented by the following general formula (14):

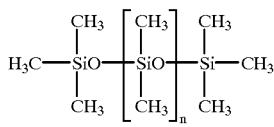

(14)

(n denotes an integer 0–3) or the following general formula (15):

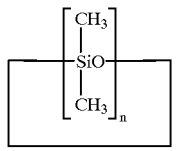

(15)

(n denotes an integer 3–8) used in the present invention are a linear chain or ring dimethyl polysiloxane, and they are volatile at normal temperatures. Examples of their product names include KF96A-0.65, KF96A-1, KF96A-1.5, KF994, KF995 and KF9937 (from Shin-Etsu Chemical Co., Ltd.). SH200-1cs, Si200-1.5cs and SH200-2cs (from Toray Dow-Corning Silicone Co., Ltd.) and TSF404, TSF405 and TSF4045 (from Toshiba Silicone Co., Ltd.).

For the volatile hydrocarbon oil whose boiling point at atmospheric pressure is 60–260° C. which is used instead of or with the aforementioned volatile silicone oil, it can be a linear chain or branched chain. Examples include Isoper (registered trademark) A, Isoper C, Isoper D, Isoper E, Isoper G, Isoper H, Isoper K, Isoper L and Isoper M (from Exxon Corporation). Shell Sol (registered trademark) 71 (from Shell Chemical Company), Soltorol (registered trademark) 100, Soltorol 130 and Soltorol 220 (from Philip Corporation), Isosol (registered trademark) 400 (from Nippon Petrochemical Co., Ltd.), Polysynlane (registered trademark) 4 (from Nippon Oil and Fats Co., Ltd.), IP Solvent (registered trademark) 1620 and IP Solvent 2028 (from Idemitsu Petrochemical Co., Ltd.), Isohexadecane and Tetraisobutane 90 (from Bayer AG), Permethyl (registered trademark) 99A, Permethyl 101A and Permethyl 102A (from Presperse Inc.). These are volatile at normal temperatures.

The amount of the volatile silicone oil and/or volatile hydrocarbon oil to be blended in the present invention is in the range of 2–98 wt %, depending on whether the product is in a stick form, a liquid form, etc. A preferable range is 5–70 wt %, and a more preferable range is 5–50 wt %. If it is less than 2 wt %, then the organic silicone resin cannot be dissolved and blended into the product.

Rf in the perfluoroalkyl denaturated silicone used in the present invention represented by the following general formula (16):

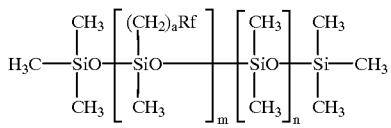

(16)

(Rf denotes a perfluoroalkyl group with a carbon number of 1–12, a is an integer 0–5, and m and n are average numbers wherein m is 1–150 and n is 0–500) is a perfluoro group with a carbon number of 1–12 and may either be a linear chain or branched chain. Examples include trifluoromethyl, pentafluoromethyl, heptafluoropropyl, nonafluorobutyl, tridecafluorohexyl, heptafluorooctyl, 2-pentafluoroethyldodecafluorohexyl, $C_{10}F_{21}$ and $C_{12}F_{25}$.

When perfluoroalkyl groups are long and m/m+n is large, the ratio of the fluorine group in the molecule becomes high and the water resistance and the oil resistance improve, but solubility in other oil components becomes poor. Selection of m, n and the perfluoro group in Rf depends on the degree of the water resistance and the oil resistance required of the product, solubility in other oil components used in the product, etc. For example, a preferable choice is something which dissolves in the volatile silicone oil and or the volatile hydrocarbon oil, but does not dissolve in the organic silicone resin. That is, it is dissolved in the volatile silicone oil and/or the volatile hydrocarbon oil in the product to improve the stability of the product and allow easy application on the lips, and, alter application on the lips, these volatile oil components evaporate and the organic silicone resin forms a thin film on the lips to prevent the secondary adhesion on coffee cups, clothes, etc. and color fading, thus improving the long-lasting effect. After the volatile oil components evaporate, phase separation brings out the perfluoroalkyl denaturated silicone oil on top of the organic silicone resin film to give a gloss to the lips.

Rf in the perfluoroalkyl denaturated methylphenyl polysiloxane used in the present invention represented by the following general formula (17):

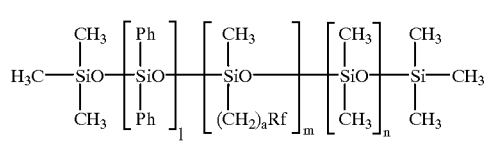

(17)

(Rf denotes a perfluoroalkyl group with a carbon number of 1–12, a is an integer 0–5, and l, m and n are average numbers wherein l is 150, m is 1–150 and n is 0–150) is a perfluoro group with a carbon number of 1–12 and may either be a linear chain or branched chain. Examples include trifluoromethyl, pentafluoromethyl, heptafluoropropyl, nonafluorobutyl, tridecafluorohexyl, heptafluorooctyl, 2-pentafluoroethyl-dodecafluorohexyl, $C_{10}F_{21}$ and $C_{12}F_{25}$.

When perfluoroalkyl groups are long and m/m+n is large, the ratio of the fluorine group in the molecule becomes high and the water resistance and the oil resistance improve, but solubility in other oil components becomes poor. When l l+m+n is large, then the phenyl group content becomes high and solubility in other hydrocarbon oil components becomes high: the glossiness also improves. Selection of l, m, n and the perfluoro group in Rf depends on the degree of the water resistance and the oil resistance required of the product, solubility in other oil components used in the product. etc. For example, a preferable choice is something which dissolves in the volatile silicone oil and/or the volatile hydrocarbon oil, but does not dissolve in the organic silicone resin. That is, it is dissolved in the volatile silicone oil and or the volatile hydrocarbon oil in the product to improve the stability of the product and allow easy application on the lips, and, after application on the lips, these volatile oil components evaporate and the organic silicone resin forms a thin film on the lips to prevent the secondary adhesion on coffee cups, clothes, etc. and color fading, thus improving the long-lasting effect. After the volatile oil components evaporate, phase separation brings out the perfluoroalkyl denaturated silicone oil on top of the organic silicone resin film to give a gloss to the lips.

The amount of the perfluoroalkyl denaturated silicone oil and/or the perfluoroalkyl denaturated methylphenyl polysiloxane to be blended in the present invention is 2–50 wt %, preferably 3–30 wt %, and more preferably 5–20 wt %. If it is less than 2 wt %, the lip gloss is insufficient. If it is more than 50 wt %, then stickiness deteriorates the feel of touch.

In addition to the aforementioned essential ingredients to obtain the effects of spreading smoothly and being easily applied to the lips, not being sticky, having a nice gloss on the lips, having a long lasting cosmetic effect, and not causing color transfer onto coffee cups, clothes, etc., the lipstick composition of the present invention can contain other ingredients normally used in cosmetics and medicinal drugs as necessary within a qualitative and quantitative range where the effects of the present invention are not degraded. Examples include ion exchange water, waxes such as carnauba wax, candelilla wax, bees wax, ceresin, microcrystalline wax and solid paraffin, oil components including various hydrocarbon oils, higher fatty acids, higher alcohols, esters, fat oils, waxes, silicone and fluorine oil such as squalane, liquid paraffin. vaseline, myristic acid, palmitic acid, stearic acid, 12-hydroxystearic acid, behenic acid, cetyl alcohol, stearyl alcohol, oleyl alcohol, batyl alcohol, cetyl-2-ethylhexanoate, 2-ethylhexyl palmitate, 2-octyldedecyl myristate, neopentyl glycol-2-ethylhexanoate, glyceryl trioctanoate, pentaerythritol tetraoctanoate, glyceryl triisostearate, glyceryl diisostearate, isopropyl myristate, myristyl myristate, glyceryl trioleate, olive oil, avocado oil, jujoba oil, sunflower oil, safflower oil, tsubaki oil, shea butter, macadamia nut oil, mink oil, lanoline, liquid lanoline, lanoline acetate, castor oil, Japanese core wax, Chinese core wax, dimethyl polysiloxane, methylphenyl polysiloxane, high polymer gum-like dimethyl polysiloxane, polyether denaturated silicone, amino denaturated silicone, high polymer gum-like amino denaturated silicone. perfluoro polyether and perfluorocarbon, humectants such as ethylene glycol, diethylene glycol, 1,3-butylene glycol, glycerine, hexamethylene glycol, isoprene glycol, polyethylene glycol, propylene glycol, dipropylene glycol, diglycerine, polyglycerine, hyaluronic acid, acetyl-hyaluronic acid, sodium chondroitin sulfate, chitin and chitosan, ultraviolet light absorbents, various surfactants, thickeners, gelating agents, metal soap, antioxidants, preservatives, drugs, pigments, dyes, pearl agent, organic powder, inorganic powders and perfumes.

The lipstick composition of the present invention is prepared by heating the composition ingredients including the aforementioned essential ingredients, stirring and mixing them, followed by cooling. The lipstick composition of the present invention can be in any form. For example, it can be solid (stick and such), semi-solid or liquid. Also, needless to say, the lipstick composition of the present invention can be made into a water-in-oil or oil-in-water type emulsion lipstick within the range where water repellency is maintained by blending ion exchange water, water soluble ingredients and an appropriate surfactant and using an emulsification technique.

EXAMPLES

The present invention is further described in detail below by referring to examples and comparative examples. The present invention is not limited to the following examples, and various changes can be made within the range of the object of the present invention. In the following description, the unit of the amount blended is always weight percent.

I: Examples of the Invention Described in Claims 1–5

The nonaqueous polymer dispersion in which the polymer is dispersed in a volatile silicone, used in the present invention, can be prepared as following, for example.

Preparation of Nonaqueous Polymer Dispersion A

15% of methyl methacrylate monomer, 25% of ethyl acrylate monomer, 0.1% of a polymerization initiator and 5% of a dispersion stabilizer dimethyl polysiloxane graft polymer (molecular weight approximately 150,000) were added to 54.9% of a dispersion medium decamethyl cyclopentasiloxane (n=5 in said general formula (3)) and the mixture was stirred for 10 hours at 120° C. to carry out the polymerization. The monomer removal treatment was then carried out by reducing the pressure, and the temperature was lowered down to 25° C. to obtain nonaqueous polymer dispersion A which was milk-white, had an average particle size of the dispersed polymer particles of 1 micrometer and had volatile silicone fur the dispersion medium.

Preparation of Nonaqueous Polymer Dispersion B

10% of methyl methacrylate monomer, 15% of ethyl acrylate monomer, 5% of methacrylic silicone ester monomer, 15% of sucrose benzoate (where 6.5–8 of 8 hydrogen atoms in hydroxyl groups of sucrose were replaced by benzoyl groups), 0.1% of a polymerization initiator and 5% of a dispersion stabilizer dimethyl polysiloxane graft polymer (molecular weight approximately 100,000) are added to 49.9% of a dispersion medium decamethyl cyclopentasiloxane (n=5 in said general formula (3)) and the mixture was stirred for 10 hours at 120° C. to carry out the polymerization. The monomer removal treatment and ethyl acetate removal treatment were then carried out by reducing the pressure, and the temperature was lowered down to 25° C. to obtain nonaqueous polymer dispersion B which was milk-white, had a average particle size of the dispersed polymer particles of 0.6 micrometer and had volatile silicone for the dispersion medium.

Examples 1–3, Comparative Examples 1–4

Ingredients of each recipe shown in Table 1 were heated up to 85° C., stirred and mixed, put into an air-tight lipstick container and cooled down to 5° C. to obtain a lipstick composition. In Table 1. said A and B were used for the nonaqueous polymer dispersion of claims 1–3 of the present invention. For the perfluoroalkyl denaturated silicone, said general formula (1), where a=8, m-11 and n=75, was used. Also in Table 1, substances blended in examples 1–4 (notes 1–4) of said Tokko Sho 61-12884 were used for the nonaqueous polymer dispersion of the comparative examples. For other ingredients, those generally available on the market as cosmetic raw materials were used.

TABLE 1

|  | Example 1 | Example 2 | Example 3 | Comparative example 1 | Comparative example 2 | Comparative example 3 | Comparative example 4 |
|---|---|---|---|---|---|---|---|
| Nonaqueous polymer dispersion A of the present invention | 50 | — | — | — | — | — | — |
| Nonaqueous polymer dispersion B of the present invention | — | 50 | 50 | — | — | — | — |
| Nonaqueous polymer dispersion of Tokko Sho 61-12884 (note 1) | — | — | — | 50 | — | — | — |
| Nonaqueous polymer dispersion of Tokko Sho 61-12884 (note 2) | — | — | — | — | 50 | — | — |
| Nonaqueous polymer dispersion of Tokko Sho 61-12884 (note 3) | — | — | — | — | — | 50 | — |
| Nonaqueous polymer dispersion of Tokko Sho 61-12884 (note 4) | — | — | — | — | — | — | 50 |
| Perfluoroalkyl modified silicone | 5 | 10 | 20 | — | — | — | — |
| Ceresin wax | 10 | 10 | 10 | 10 | 10 | 10 | 10 |
| Candelilla wax | 2 | 2 | 2 | 2 | 2 | 2 | 2 |
| Decamethyl cyclopentasiloxane | 23 | 18 | 8 | — | — | — | — |
| Isoper H | — | — | — | 28 | 28 | 28 | 28 |
| Methylphenyl polysiloxane (15CS) | 7 | 7 | 7 | 7 | 7 | 7 | 7 |
| Red pigment Lithol Rubin BCA | 3 | 3 | 3 | 3 | 3 | 3 | 3 |
| Perfume | Appropriate amount | Appropriate amount | Appropriate amount | Appropriate amount | Appropriate amount | Appropriate amount | Appropriate amount |

(Note 1): Nonaqueous polymer dispersion used in (mascara) (dispersed polymer: methyl acrylate polymer, medium: mineral spirit)
(Note 2): Nonaqueous polymer dispersion used in (eyeliner) (dispersed polymer: ethyl acrylate polymer, medium: Isoper)
(Note 3): Nonaqueous polymer dispersion used in (eyeliner) (dispersed polymer: vinyl acetate polymer, medium: Isoper)
(Note 4): Nonaqueous polymer dispersion used in (nail enamel) (dispersed polymer: vinyl acetate-acrylic acid copolymer, medium: ethanol)

Examples 4–6

Lipstick compositions were prepared in the same manner as in Examples 1–3 of Table 1 with the same ingredients except for the fact that perfluoroalkyl denaturated silicone was replaced by perfluoroalkyl denaturated methylphenyl polysiloxane represented by said general formula (2) wherein a=2, l=8, m=6, n=40 and the carbon number of Rf is 8. These were called Examples 4–6 respectively.

Evaluation of the Lipstick Compositions

The actions and effects of the lipstick compositions of each example and comparative example were evaluated with usage testing by a ten person panel. Evaluation items included ease of application odor at the time of application, stickiness (immediately to 3 hours after applications, gloss (5 minutes to 3 hours after application) and color transfer onto coffee cups and clothes (5 minutes to 3 hours after application). Evaluation standards were defined as follows.

Evaluation Standards

☆: All 10 panelers rated very good.

◉: 8 or more of 10 panelers rated good.

○: 6 or more of 10 panders rated good.

Δ: 4 or more of 10 panders rated good.

×: 3 or less of 10 panelers rated good. The evaluation results are shown in Table 2.

TABLE 2

|  | Example | | | | | | Comparative example | | | |
|---|---|---|---|---|---|---|---|---|---|---|
|  | 1 | 2 | 3 | 4 | 5 | 6 | 1 | 2 | 3 | 4 |
| Ease of application | ○ | ○ | ◉ | ○ | ○ | ◉ | ○ | ○ | ○ | ○ |
| Odor at the time of application | ◉ | ◉ | ◉ | ◉ | ◉ | ◉ | × | Δ | Δ | Δ |
| Stickiness (immediately to 3 hours after application) | ○ | ○ | ◉ | ○ | ○ | ◉ | Δ | Δ | Δ | Δ |
| Gloss (5 minutes to 3 hours after application) | ○ | ◉ | ◉ | ◉ | ◉ | ☆ | Δ | Δ | × | Δ |

TABLE 2-continued

|  |  | Example | | | | | | Comparative example | | | |
|---|---|---|---|---|---|---|---|---|---|---|---|
|  |  | 1 | 2 | 3 | 4 | 5 | 6 | 1 | 2 | 3 | 4 |
| Color transfer onto coffee cups and clothes (long lasting effect) | 5 minutes after application | ○ | ○ | ⊚ | ○ | ○ | ⊚ | Δ | Δ | Δ | Δ |
|  | 3 hours after application | ○ | ○ | ⊚ | ○ | ⊚ | ⊚ | ○ | ○ | Δ | Δ |

As shown in Table 2, the lipstick compositions of Example 1, Example 2 and Example 3 of the present invention which contain nonaqueous polymer dispersions A and B with volatile silicone as a dispersion medium are superior in terms of odor at the time of application, stickiness (immediately to 3 hours after application), gloss (5 minutes to 3 hours after application) and color transfer onto coffee cups and clothes (5 minutes after application), compared with the lipstick compositions of Comparative examples 1–4 which contain 4 types of nonaqueous polymer dispersions described in examples of Tokko Sho 61-12884. It is also shown that Example 3, in which 20 wt % of perfluoroalkyl denaturated silicone is blended into nonaqueous polymer dispersion B, is superior in terms of stickiness (immediately to 3 hours after application) and color transfer onto coffee cups and clothes (5 minutes and 3 hours after application), compared with Example 1 in which 5 wt % of perfluoroalkyl denaturated silicone is blended and Example 2 in which 10 wt % is blended. It is also shown that Example 6, in which 20 wt % of perfluoroalkyl denaturated methylphenyl polysiloxane is blended into nonaqueous polymer dispersion B, is superior in terms of stickiness (immediately to 3 hours after application) and color transfer onto coffee cups and clothes (5 minutes and 3 hours after application), compared with Example 4 in which 5 wt % of perfluoroalkyl denaturated methylphenyl polysiloxane is blended and Example 5 in which 10 wt % is blended, and that Example 6 is even superior to Example 3 in terms of gloss (5 minutes to 3 hours after application).

II: Examples of the Invention Described in Claims 6 and 7

Examples 7–10, Comparative Examples 5–7

Ingredients of each recipe shown in Table 3 were heated up to 85° C. stirred and mixed, put into an air-tight lipstick container and cooled down to 5° C. to obtain a lipstick composition.

TABLE 3

|  | Example | | | | Comparative example | | |
|---|---|---|---|---|---|---|---|
|  | 7 | 8 | 9 | 10 | 5 | 6 | 7 |
| Organic silicone resin (note 1) | 25 | 25 | 25 | 35 | 25 | — | — |
| Dimethyl polysiloxane (100 CS/25° C.) | — | — | — | — | — | 25 | 25 |
| Decamethyl cyclopentasiloxane | 43 | 38 | 28 | 18 | 38 | 38 | 38 |
| Isosol 400 | — | — | — | 10 | — | — | — |
| Ceresin | 10 | 10 | 10 | 10 | 10 | 10 | 10 |
| Candelilla wax | 2 | 2 | 2 | 2 | 2 | 2 | 2 |
| Perfluoroalkyl modified silicone (note 2) | 5 | 10 | 20 | 10 | — | 10 | — |
| Dimethyl polysiloxane (20 CS/25° C.) | — | — | — | — | 10 | — | 10 |
| Glyceryl diisostearate | 12 | 12 | 12 | 12 | 12 | 12 | 12 |
| Red pigment Lithol Rubin BCA | 3 | 3 | 3 | 3 | 3 | 3 | 3 |
| Perfume | Appropriate amount | Appropriate amount | Appropriate amount | Appropriate amount | Appropriate amount | Appropriate amount | Appropriate amount |

(Note 1) Organic silicone resin with a molecular weight of approximately 3,000 represented by the average formula $(CH_3)_{3.33}$—$SiO_{1.3}$ with $(CH_3)_3SiO_{1/2}$ unit $SiO_2$ unit = 0.8.1.0.
(Note 2) Perfluoroalkyl denaturated silicone represented by the general formula (16) wherein Rf is a heptadecafluorooctyl group, a = 2, m = 11 and n = 75.

Examples 11–14, Comparative Examples 8–10

Ingredients of each recipe shown in Table 4 were heated up to 85° C., stirred and mixed, put into an air tight, lipstick container and cooled down to 5° C. to obtain a lipstick composition.

TABLE 4

|  | Example | | | | | Comparative example | | |
| --- | --- | --- | --- | --- | --- | --- | --- | --- |
|  | 11 | 12 | 13 | 14 | 15 | 8 | 9 | 10 |
| Organic silicone resin (note 3) | 5 | 10 | 20 | 30 | 30 | 30 | — | — |
| Dimethyl polysiloxane (100 CS/25° C.) | — | — | — | — | — | — | 30 | 30 |
| Decamethyl cyclopentasiloxane | 58 | 53 | 43 | 23 | 23 | 33 | 33 | 33 |
| Isosol 400 | — | — | — | 10 | 10 | — | — | — |
| Ceresin | 10 | 10 | 10 | 10 | 10 | 10 | 10 | 10 |
| Candelilla wax | 2 | 2 | 2 | 2 | 2 | 2 | 2 | 2 |
| Perfluoroalkyl modified silicone (note 4) | 0 | 0 | 0 | 0 | 10 | 0 | 0 | 0 |
| Perfluoroalkyl modified methylphenyl polysiloxane (note 5) | 20 | 20 | 20 | 20 | 10 | — | 20 | — |
| Dimethyl polysiloxane (20 CS/25° C.) | — | — | — | — | — | 20 | — | 20 |
| Methylphenyl polysiloxane (14 CS/25° C.) | 2 | 2 | 2 | 2 | 2 | 2 | 2 | 2 |
| Red pigment Lithol Rubin BCA | 3 | 3 | 3 | 3 | 3 | 3 | 3 | 3 |
| Perfume | Appropriate amount | Appropriate amount | Appropriate amount | Appropriate amount | Appropriate amount | Appropriate amount | Appropriate amount | Appropriate amount |

(Note 3) Organic silicone resin with a molecular weight of approximately 5,000 represented by the average formula $(CH_3)_{1.8}SiO_{1.1}$ with $(CH_3)_2SiO_{1/2}$ unit $SiO_2$ unit = 1.5/1.0.
(Note 4) Perfluoroalkyl denaturated silicone represented by the general formula (16) wherein Rf is a heptadecafluorooctyl group a = 2, m = 11 and n = 75.
(Note 5) Perfluoroalkyl denaturated methylphenyl polysiloxane represented by the general formula (17) wherein Rf is a heptadecafluorooctyl group a = 2, m = 2 and n = 6.

Evaluation of the Lipstick Compositions

The actions and effects of the lipstick compositions of each example and comparative example were evaluated with usage testing by a ten specialist panel. Evaluation items included ease of application, gloss (5 minutes to 3 hours after application) and color transfer onto coffee cups and clothes (5 minutes to 3 hours after application). Evaluation standards were defined as follows.

Evaluation Standards

☆: All 10 panelers rated very good.
⊚: 8 or more of 10 panelers rated good.
○: 6 or more of 10 panelers rated good.
Δ: 4 or more of 10 panelers rated good.
×: 3 or less of 10 panelers rated good.

The evaluation results are shown in Table 5.

Example 16

(1) Solid paraffin 15.0%
(2) Ceresin 5.0
(3) Organic silicone resin (note 5) 25.0
(4) Decamethyl cyclopentasiloxane 20.0
(5) Octamethyl cyclotetrasiloxane 8.0
(6) Perfluoroalkyl denaturated silicone 10.0 (note 6)
(7) Polyether denaturated silicone (note 7) 5.0
(8) Glyceryl trioctanoate 3.0
(9) Red 201 1.5
(10) Red 202 1.5
(12) Titanium dioxide 1.0
(13) Mica coated with titanium oxide 5.0
(14) Perfume Appropriate amount

TABLE 5

|  | Example | | | | | | | | | Comparative example | | | | | |
| --- | --- | --- | --- | --- | --- | --- | --- | --- | --- | --- | --- | --- | --- | --- | --- |
|  | 7 | 8 | 9 | 10 | 11 | 12 | 13 | 14 | 15 | 8 | 9 | 10 | 11 | 12 | 13 |
| Base of application | ⊚ | ⊚ | ○ | ○ | ⊚ | ⊚ | ⊚ | ○ | ⊚ | ⊚ | ⊚ | ⊚ | ○ | ⊚ | ⊚ |
| Gloss (5 minutes to 3 hours after application) | ○ | ⊚ | ☆ | ⊚ | ○ | ○ | ○ | ⊚ | ⊚ | × | ○ | × | × | ○ | Δ |
| Color transfer onto coffee cups and clothes 5 minutes after application | ○ | ⊚ | ○ | ⊚ | ○ | ○ | ○ | ⊚ | ⊚ | × | Δ | × | × | Δ | × |
| Color transfer onto coffee cups and clothes 3 hours after application | ⊚ | ⊚ | ⊚ | ⊚ | ○ | ○ | ⊚ | ☆ | ⊚ | × | Δ | × | × | Δ | × |

As shown in Table 5 the lipstick compositions of the present invention are superior in terms of ease of application, gloss after application and long-lasting effect, exhibited by less color transfer onto coffee cups and clothes, compared with the comparative examples.

(Note 5) Organic silicone resin with a molecular weight of approximately 10,000 represented by the average formula $(CH_3)_{1.23}(C_6H_5)_{0.18}SiO_{1.30}$ with $(CH_3)_3SiO_{1/2}$ unit/$(C_6H_5SiO$ unit/$(C_6H_5)_2SiO_{3/2}$ unit/$SiO_2$ unit=0.9/0.1/0.2/1.0.

(Note 6) Perfluoroalkyl denaturated silicone represented by the general formula (16) wherein Rf is a nonafluorobutyl group, a=2, m=25 and n=200.

(Note 7) KF6008 (from Shin-Etsu Chemical Co., Ltd.)

The materials (1)–(8) and (14) were heated and dissolved, and then the materials (9)–(13) were mixed and dispersed into them. After thorough deaeration, the mixture was put into a prescribed metal mold and cooled to obtain a lipstick.

This lipstick spread smoothly and was easily applied on the lips, was not sticky, had a nice gloss on the lips, and had a long lasting cosmetic effect wherein color did not transfer onto coffee cups, clothes, etc.

Example 17

(1) Ceresin 4.0%
(2) Candelilla wax 8.0
(3) Carnauba wax 2.0
(4) Organic silicone resin (note 8) 10.0
(5) Decamethyl cyclopentasiloxane 54.95
(6) Perfluoroalkyl denaturated methylphenyl 3.0 polysiloxane (note 9)
(7) Methylphenyl polysiloxane (15CS,25° C.) 2.0
(8) POE (25) POP (20) tetradecyl ether 1.0
(9) Ion exchange water 5.0
(10) Glycerine 2.0
(11) Propylene glycol 1.0
(12) Titanium dioxide 4.5
(13) Red 201 0.5
(14) Red 202 2.0
(15) Red 223 0.05
(16) Ultraviolet light absorbent Appropriate amount
(17) Antioxidant Appropriate amount
(18) Perfume Appropriate amount (Note 8) Organic silicone resin with a molecular weight of approximately 20,000 represented by the average formula $(CH_3)_{1.8}SiO_{1.1}$ with $(CH_3)_3SiO_{1/2}$ unit $SiO_2$ unit-0.5/1.

(Note 9) Perfluoroalkyl denaturated methylphenyl polysiloxane represented by the general formula (17) wherein Rf is $C_{12}F_{26}$, a=2, l=40, m=20 and n=100.

The materials (13)–(15) were thoroughly stirred and mixed and then added to the heated and dissolved materials (1)–(8) and (16)–(18) (oil phase). Separately, the materials (9) and (11) were heated and dissolved (water phase). The water phase was added to the oil phase and, after emulsification with a homogenizer the mixture was poured into a mold and quickly cooled to obtain a lipstick.

This lipstick spread smoothly and was easily applied on the lips, was not sticky, had a nice gloss on the lips, and had a long lasting cosmetic effect wherein color did not transfer onto coffee cups, clothes, etc.

Example 18

(1) Organic silicone resin (note 10) 40.0%
(2) Decamethyl cyclopentasiloxane 13.0
(3) Octamethyl cyclotetrasiloxane 13.0
(4) Perfluoroalkyl denaturated silicone 20.0 (note 11)
(5) Glyceryl trioctanoate 3.0
(6) Spherical silicone rubber powder 5.0
(7) Red 201 1.5
(8) Red 202 1.5
(9) Titanium dioxide 3.0
(10) Perfume Appropriate amount (Note 10) Organic silicone resin with a molecular weight of approximately 3,000 represented by the average formula $(CH_3)_{1.33}SiO_{1.3}$ with $(CH_3)_3SiO_{1/2}$ unit/$SiO_2$ unit=0.8/1.0.

(Note 11) Perfluoroalkyl denaturated silicone represented by the general formula (16) wherein Rf is a heptadecafluorooctyl group. a=2, m=11 and n=75.

The materials (1)–(5) and (10) were heated and dissolved, and then the materials (6)–(9), mixed and stirred, were added, followed by thorough mixing. The mixture was then put into a container to obtain a liquid lipstick.

This lipstick spread smoothly and was easily applied on the lips, was not sticky, had a nice gloss on the lips, and had a long lasting cosmetic effect wherein color did not transfer onto coffee cups, clothes, etc.

Example 19

(1) Ceresin 4.0%
(2) Candelilia wax 8.0
(3) Carnauba wax 2.0
(4) Organic silicone resin (note 8) 10.0
(5) Decamethyl cyclopentasiloxane 54.95
(6) Perfluoroalkyl denaturated methylphenyl 3.0 polysiloxane (note 9)
(7) Perfluoroalkyl denaturated silicone 1.0 (note 10)
(8) Methylphenyl polysiloxane (15CS/25° C.) 2.0
(9) POE (25) POP (20) tetradecyl ether 1.0
(10) Ion exchange water 5.0
(11) Glycerine 2.0
(12) Propylene glycol 1.0
(13) Titanium dioxide 4.5
(14) Red 201 0.5
(15) Red 202 2.0
(16) Red 223 0.05
(17) Ultraviolet light absorbent Appropriate amount
(18) Antioxidant Appropriate amount
(19) Perfume Appropriate amount (Note 8) Organic silicone resin with a molecular weight of approximately 20,000 represented by the average formula $(CH_3)_{1.8}SiO_{1.1}$ with $(CH_3)_3SiO_{1/2}$ unit/$SiO_2$ unit= 0.5/1.

(Note 9) Perfluoroalkyl denaturated methylphenyl polysiloxane represented by the general formula (17) wherein Rf is $C_{12}F_{25}$, a=2, l=40, m=20 and n=100.

(Note 10) Perfluoroalkyl denaturated silicone represented by the general formula (16) wherein Rf is a nonafluorobutyl group, a=2, m=25 and n=200.

The materials (14)–(16) were thoroughly stirred and mixed and then added to the heated and dissolved materials (1)–(9) and (17)–(19) (oil phase). Separately, the materials (10) and (12) were heated and dissolved (water phase). The water phase was added to the oil phase and, after emulsification with a homogenizer, the mixture was poured into a mold and quickly cooled to obtain a lipstick.

This lipstick spread smoothly and was easily applied on the lips, was not sticky, had a nice gloss on the lips, and had a long lasting cosmetic effect wherein color did not transfer onto coffee cups, clothes, etc.

What is claimed is:

1. A lipstick composition containing a nonaqueous polymer dispersion capable of forming a film in which polymer is dispersed in a volatile silicone and perfluoroalkyl denaturated silicone represented by the following general formula (1):

(1)

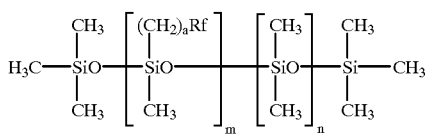

where, Rf denotes a perfluoroalkyl group with a carbon number of 1–12, a is an integer 0–5, and m and n are average numbers wherein m is 1–500 and n is 0–500.

2. A lipstick composition containing a nonaqueous polymer dispersion capable of forming a film in which the polymer is dispersed in a volatile silicone and perfluoroalkyl denaturated methylphenyl polysiloxane represented by the following general formula (2):

(2)

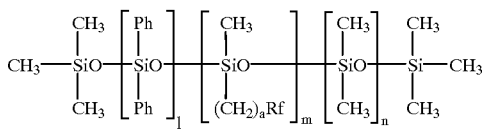

where, Rf denotes a perfluoroalkyl group with a carbon number of 1–12, a is an integer 0–5, and l, m and n are average numbers wherein l is 1 –150, in is 1–150 and n is 0–150.

3. The lipstick composition of claim 1 wherein said nonaqueous polymer dispersion contains a polymer of an acrylic ester or methacrylic ester or a copolymer of an acrylic ester and methacrylic ester.

4. The lipstick composition of claim 1 wherein said nonaqueous polymer dispersion additionally has sucrose benzoate dispersed in it.

5. The lipstick composition of claim 1 wherein said volatile silicone is selected from the group consisting of one or more volatile silicones represented by the following general formula (3):

(3)

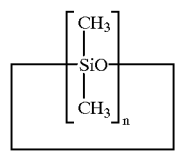

where n denotes an integer 3–7, or the following general formula (4):

(4)

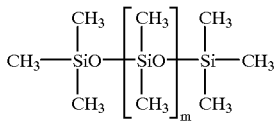

where n denotes an integer 0–5.

6. A lipstick composition containing 1–70 wt % of organic silicone resin represented by the following average formula (5):

$R_nSiO_{(4-n)/2}$ (5)

wherein R denotes a hydrocarbon group with a carbon number of 1–6 or a phenyl group, and n denotes a value in the range of 1.0–1.8; 2–98 wt % of volatile silicone oil represented by the following general formula (6):

(6)

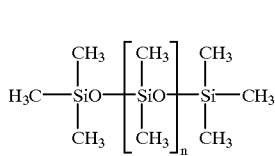

wherein n denotes an integer 0–3; or the following general formula (7):

(3)

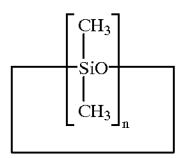

wherein n denotes an integer 3–8; and or volatile hydrocarbon oil whose boiling point at the atmospheric pressure is 60–260° C. and 2–50 wt % of perfluoroalkyl denaturated silicone represented by the following general formula (8):

(8)

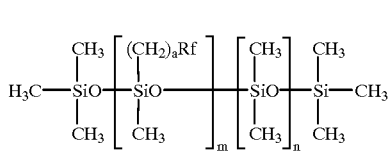

wherein Rf denotes a perfluoroalkyl group with a carbon number of 1–12, a is an integer 0–5, and m and n are average numbers wherein m is 1–150 and n is 0–500.

7. A lipstick composition containing 1–70 wt % of organic silicone resin represented by the following average formula (9):

$R_nSiO_{(4-n)/2}$ (9)

wherein R denotes a hydrocarbon group with a carbon number of 1–6 or a phenyl group, and n denotes a value in the range of 1.0–1.8; 2–98 wt % of volatile silicone oil represented by the following general formula (10):

(10)

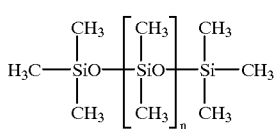

wherein n denotes an integer 0–3; or the following general formula (11)

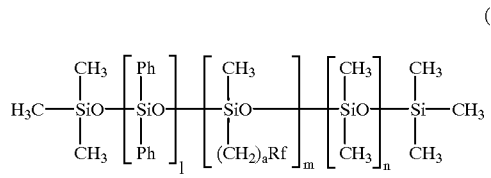

(12)

wherein n denotes an integer 3–8; and or volatile hydrocarbon oil whose boiling point at the atmospheric pressure is 60–260° C. and 2–50 wt % of perfluoroalkyl denaturated methylphenyl polysiloxane represented by the following general formula (12):

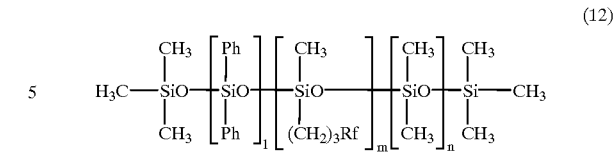

(12)

wherein Rf denotes a perfluoroalkyl group with a carbon number of 1–12, a is an integer 0–5, and l, m and n are average numbers wherein l is 1–150, m is 1–150 and n is 0–150.

* * * * *